Figure 1:
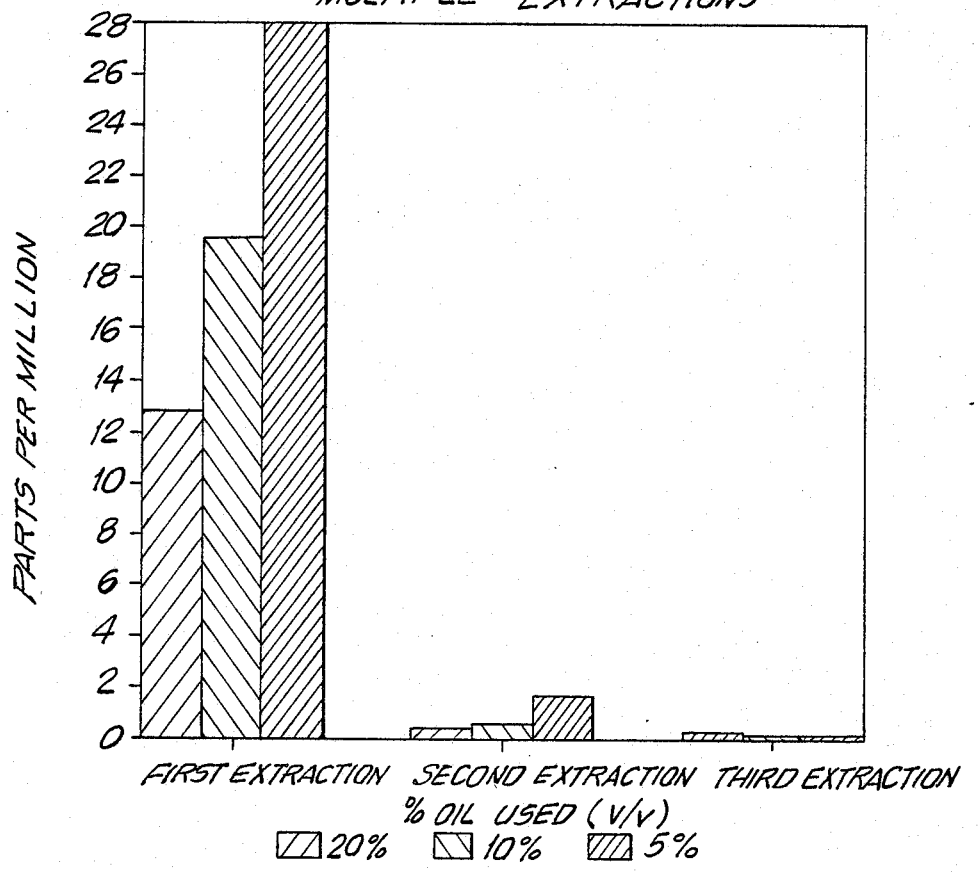

United States Patent [19]

Woods et al.

[11] Patent Number: 4,789,545

[45] Date of Patent: Dec. 6, 1988

[54] REMOVAL OF LIPID SOLUBLE PROCESS CHEMICALS FROM BIOLOGICAL MATERIALS BY EXTRACTION WITH NATURALLY OCCURRING OILS OR SYNTHETIC SUBSTITUTES THEREOF

[75] Inventors: Kenneth R. Woods, Sea Cliff; Thomas W. Orme, Huntington Station, both of N.Y.

[73] Assignee: New York Blood Center, Inc., New York, N.Y.

[21] Appl. No.: 846,374

[22] Filed: Mar. 31, 1986

[51] Int. Cl.$^4$ .................... A61K 35/14; A61K 39/12; A01N 1/02; C12N 7/06

[52] U.S. Cl. .................... 424/101; 424/89; 435/2; 435/238; 514/802

[58] Field of Search .................. 424/89, 101; 514/802; 435/2, 238

[56] References Cited

U.S. PATENT DOCUMENTS

| | | | |
|---|---|---|---|
| 3,647,624 | 3/1972 | Evenson | 435/2 |
| 3,682,835 | 8/1972 | Louderback | 424/101 |
| 4,314,997 | 2/1982 | Shanbrom | 424/101 |
| 4,481,189 | 11/1984 | Prince | 424/101 |
| 4,522,809 | 6/1985 | Adamowicz et al. | 435/238 |
| 4,534,972 | 8/1985 | Lembach | 514/802 |
| 4,540,573 | 9/1985 | Neurath | 424/85 |
| 4,615,886 | 10/1986 | Purcell et al. | 424/101 |
| 4,647,536 | 3/1987 | Mosbach et al. | 424/93 |

FOREIGN PATENT DOCUMENTS

| | | |
|---|---|---|
| 56-127308 | 10/1981 | Japan .................... 424/101 |
| 0050061 | 4/1982 | United Kingdom . |
| 8304371 | 12/1983 | World Int. Prop. O. . |

OTHER PUBLICATIONS

Chemical Abstracts, vol. 96, No. 13, 29th Mar. 1982, p. 516, abstract no. 101990k, Columbus, Ohio, US; N. Shibata et al.: "Efficient elimination of lipid-soluable toxic substances by silicone oil hemodialysis", & Med. J. Osaka Univ. 1981, 32(1–2), 1–10.

Chemical Abstracts, vol. 77, No. 11, 11th Sep. 1972, pp. 234–235, abstract no. 7231w, Columbus, Ohio, US; M. A. Evenson et al.: "Direct-contact (membraneless) hemoperfusion through oils", & Clin. Chem. 1972, 18(6), 554–562.

F. W. Hartman, G. A. LoGrippo, "Combined beta--Propiolactone and Ultraviolet Irradiation for Plasma Sterilization", Hepatitis Frontiers, Henry Ford Hospital International Symposium, Brown & Co. (1957), 407–416.

D. Heinrich and H. Berthold, "Application of Cold Sterilized Prothrombin Complex Concentrates in Man, Clinical and Serological Studies", XIII International Congress of the World Federation of Hemophilia, Tel Aviv, Jul. 8–13, 1979.

R. Kotitschke, W. Stephen, "Kominierte Behandlung von Gerinnungsfaktoren in Humanplasma mit B-Propiolacton and UV. Struktur und Funktion des Fibrinogens", H. Schroeer, G. Hauck, F. Zimmerman et al, eds. *Blutgerinnung und Mikrozirkulation Stuttgart:* Verlag (1976), 222–228.

Von. N. Heimburger, H. Schwinn, P. Gratz et al, "Faktor VIII–Konzentrate, Hochgereinigt und in Losung Erhitzt, "*Arzneim-Thromb/Drug Res.* (1981), 31, 619.

N. Heimburger, H. Schwinn, R. Mauler, "Factor VIII Concentrate, Hepatitis-Safe: Progress in the Treatment of Hemophilia A", *Die gelben Hefte* (1980), 20, 165–174.

(List continued on next page.)

Primary Examiner—Ronald W. Griffin
Assistant Examiner—Nancy S. Carson
Attorney, Agent, or Firm—Sprung Horn Kramer & Woods

[57] ABSTRACT

A method of removing lipid soluble process chemicals from biological materials containing the lipid soluble process chemicals comprising bringing the biological materials containing the lipid soluble process chemicals into contact with an effective amount of a naturally occurring oil extracted from a plant or an animal or a synthetic compound of similar chemical structure, agitating the resultant mixture, separating out an upper-phase and a lower-phase by sedimentation and decanting the upper-phase. The method is particularly useful for producing relatively virus free physiologically acceptable plasma.

14 Claims, 2 Drawing Sheets

OTHER PUBLICATIONS

E. Tabor, D. L. Aronson, R. J. Gerety, "Removal of Hepatitis B Virus Infectivity from Factor IX Complex by Hepatitis B Immune Globulin", *Lancet* (1980), 2, 68–70.

H. G. J. Brummelhuis, J. Over, L. A. Duivis—Vorst et al, "Contributions to the Optimal Use of Human Blood. IX Elimination of Hepatitis B Transmission by (Potentially) Infectious Plasma Derivatives", *Vox San* (1983), 45, 205–216.

J. W. Oliphant, A Hollaender, "Homologous Serum Jaundice Experimental Inactivation of Etiologic Agent in Serum by Ultraviolet Irradiation", *Public Health Rep.* (1945), 61, 598–602.

F. O. MacCallum, "Homologous Serum Hepatitis", *Proc. Roy. Soc. Med.* (1946), 39, 655.

R. Murray, J. W. Oliphant, J. T. Tripp et al, "Effect of Ultraviolet Radiation on the Infectivity of Icterogenic Plasma," *JAMA* (1955), 157, 8–14.

G. A. LoGrippo, H. Hayashi, "Efficacy of beta—Propiolactone with Ultra violet Irradiation of Hepatitis B Antigen in Human Plasma Pools", *Henry Ford Hosp. Med. J.* (1973), 21, 181–186.

D. Heinrich, H. Berthold, "Application of Cold Sterilized Prothrombin Complex Concentrates in Man: Clinical and Serological Studies", The 13th International Congress of the World Federation of Hemophilia, Tel Aviv, Jul. 8–13, 1979.

W. Stephen, A. M. Prince, "Efficacy of Combined Treatment of Factor IX Complex (PPSB) with $\beta$—Propiolactone (b—PL) and Ultraviolet (UV) Irradiation", *Haemostatis.* (1981), 10, 67.

A. M. Prince, W. Stephan, B. Brotman, "$\beta$-Propiolactone/Ultraviolet Irradiation: A Review of its Effectiveness for Inactivation of Viruses in Blood Derivatives", *Rev. Infect. Dis.* (1983), 5, 92–107.

W. Stephen, A. M. Prince and R. Kotitschke, "Factor VIII Concentrate from Cold Sterilized Human Plasma", *Develop Biol. Stand* (1983), 54, 491.

S. S. Gellis, J. R. Neefe, J. Stokes Jr. et al, "Chemical, Clinical and Immunological Studies on the Products of Human Plasma Fractionation XXXVI Inactivation of the Virus of Homologous Serum Hepatitis in Solutions of Normal Human Serum Albumin by Means of Heat", *J. Clin. Invest.* (1948), 27, 239–244.

R. Murray, W. C. L. Diefenbach, "Effect of Heat on the Agent of Homologous Serum Hepatitis", *Proc. Soc. Exp. Biol. Med.* (1953), 84, 230–231.

J. P. Soulier, C. Blatix, A. M. Courouce et al., "Prevention of Virus B Hepatitis (SH Hepatitis)", *Am. J. Dis. Chid.* (1972), 123, 429–434.

T. Shikata, T. Karasawa, K. Abe et al, "Incomplete Inactivation of Hepatitis B Virus After Heat—Treatment at 60° C. for 10 hours", *J. Infect. Dis.* (1978), 138, 242–244.

E. Tabor, R. J. Gerety, "The Chimpanzee Animal Model for non-A non-B Hepatitis: New Applications", W. Szmuness, H. J. Alter, J. E. Maynard eds. *Viral Hepatitis: 1981 International Symposium.*, Philadelphia: The Franklin Press (1981), 305–317.

E. Tabor, G. Murano, P. Snoy et al, "Inactivation of Hepatitis B Virus by Heat in Antithrombin III Stabilized with Citrate", *Thromb Res.* (1981), 22, 233–238.

D. Menache, D. L. Aronson, "Measures to Inactivate Viral Contaminants of Pooled Plasma Products", R. Y. Dodd, L. F. Baker eds. *Infection Immunity and Blood Transfusion Proc. XVII Annual Scientific Symposium*, May 9–11, 1984. New York, Alan R. Loss (1985), 407–423.

G. Dolana, D. Tse, W. Thomas et al, "Hepatitis Risk Reduction in Hemophilia: A Heated Factor VIII Preparation", *J. Amer. Soc. Hematol.* (1982), 60 (Supp 1), 2102.

F. R. Hollinger, G. Dolana, W. Thomas et al, "Reduction of Infectivity of Hepatitis B Virus (HBV) and a non-A, non-B Hepatitis Agent by Heat Treatment of Human Antihemophilic Factor (AHF) Concentrates", L. R. Overbyk F. Deinhardt, J. Deinhardt, eds., *Viral Hepatitis: Second International Max von Pettenkofer Symposium,* New York: Marcel Dekker, Inc. (1983) 245–246.

F. B. Hollinger, G. Dolana, W. Thomas et al, "Reduction in Risk of Hepatitis Transmission by Heat—Treatment of a Human Factor VIII Concentrate", *J. Infect. Dis.* (1984), 150, 250–262.

A. M. Prince, B. Horowitz, B. Brotman et al, "Inactivation of Hepatitis B and Hutchinson Strain non-A, non-B hepatitis Viruses by Exposure to Tween 80 and Ether", *Vox Sang* (1984), 46, 36–43.

S. M. Feinstone, K. B. Mihalik, T. Kamimura et al, "Inactivation of Hepatitis B Virus and non—A, non—B Hepatitis by Chloroform", *Infect. Immunol.* (1983), 41, 816–821.

(List continued on next page.)

OTHER PUBLICATIONS

D. W. Bradley, J. E. Maynard, H. Popper et al, "Post-transfusion non—A, non—B Hepatitis: Physiochemical Properties of Two Distinct Agents", *J. Infect. Dis.* (1983), 254–265.

A. M. Prince, B. Horowitz, B. Brotman et al, "Inactivation of Hepatitis B Virus and non–A, non–B hepatitis by Chloroform", *Infect. Immunol.* (1983), 41, 816–821.

M. Colombo, V. Carnelli, C. Gazengel, P. M. Mannucci, G. F. Savidge, K. Schimpf, "Transmission of non–A, non–B Hepatitis by Heat–Treated Factor VIII Concentrate", *Lancet* (1985), Jul. 1–4.

F. E. Preston, C. R. M. Hay, M. S. Dewar, M. Greaves, D. R. Triger, "Non–A, non–B, Hepatitis and Heat Treated Factor VIII Concentrates", *Lancet* (1985), Jul. 213.

C. Rouzioux, S. Chamaret, L. Montggnier, V. Carnelli, G. Rolland, P. M. Mannucci, "Absence of Antibodies to AIDS Virus in Haemophiliacs Treated with Heat--Treated Factor VIII Concentrate", *Lancet* (1985), Feb., 271–272.

P. B. A. Kernoff, E. J. Miller, G. F. Savidge, S. J. Machin, M. S. Dewar, F. E. Preston, "Wet Heating for Saafer Factor VIII Concentrate?", *Lancet* 1985, Sep., 271.

Y. K. Yip, R. H. L. Pang, J. O. Oppenheim, M. S. Nashbar, D. Henriksen, T. Zerebeckyj—Eckhardt, J. Vilcek, "Stimulation of Human Gamma Interferon Production by Diterpene Esters", *Infect and Immun.* (1981), 131–139.

B. D. Williamson, E. A. Carswell, B. Y. Rubin, J. S. Prendergast, H. J. Old, "Human Tumor Necrosis Factor Produced by Human B-cells Lines: Synergistic Cytoxic Interaction with Human Interferon", *Proc. Natl. Acad. Sci., USA* (1983), 80, 5397–5401.

B. Y. Rubin, S. L. Anderson, S. A. Sullivan, B. D. Williamson, E. A. Carswell, L. J. Old, "Purification and Characterization of a Human Tumor Necrosis Factor from the LukII Cell Line", *Proc. Natl. Acad. Sci., USA* (1985), 82, 6637–6641.

A. Helenius and K. Sinous, "Solubilization of Membranes by Detergents", *Biochem. Biophys. ACTA*, (1975), 415, 29–79.

FIG. 2

INACTIVATION OF VSV ADDED TO AHF BY TNBP/TRITON X-45 MIXTURE

REMOVAL OF LIPID SOLUBLE PROCESS CHEMICALS FROM BIOLOGICAL MATERIALS BY EXTRACTION WITH NATURALLY OCCURRING OILS OR SYNTHETIC SUBSTITUTES THEREOF

BACKGROUND OF THE INVENTION

The present invention concerns removal of virus attenuating chemicals and other lipid soluble process chemicals from biological materials by extraction with naturally occurring oils or synthetic substitutes thereof.

Numerous attempts have been made to inactivate viruses such as hepatitis B virus (HBV) in mammalian, especially human, blood plasma. Inactivation renders a virus non-infectious and non-pathogenic. It is the practice in some countries to effect inactivation of the hepatitis B virus in the blood plasma by bringing the plasma into contact with a viral inactivating agent which cross-links the proteinaceous portions of hepatitis B virus or which interacts with the nucleic acid of the virus. For instance, it is known that hepatitis B virus is inactivated by contact with an aldehyde, such as formaldehyde.

Procedures that have been tested for inactivating viruses in protein biologics include the following:

(1) neutralization with specific antibodies (E. Tabor, D. L. Aronson, R. J. Gerety, "Removal of Hepatitis B Virus Infectivity from Factor IX Complex by Hepatitis B Immune Globulin", *Lancet,* (1980), 2, 68–70; H. G. J. Brummelhuis, J. Over, L. A. Duivis-Vorst et al, "Contributions to the Optimal Use of Human Blood. IX->Elimination of Hepatitis B Transmission by (Potentially) Infectious Plasma Derivatives", *Vox San,* (1983), 45, 205–216), (2) ultraviolet irradiation ("UV") (J. W. Oliphant, A. Hollaender, "Homologous Serum Jaundice Experimental Inactivation of Etiologic Agent in Serum by Ultraviolet Irradiation", *Public Health Rep.,* (1945), 61, 598–602; F. O. MacCallum, "Homologous Serum Hepatitis", *Proc. Roy. Soc. Med.,* (1946), 39, 655; R. Murray, J. W. Oliphant, J. T. Tripp et al, "Effect of Ultraviolet Radiation on the Infectivity of Icterogenic Plasma, *JAMA,* (1955), 157, 8–14), (3) beta-propiolactone ("BPL") and ultraviolet (UV) radiation (F. W. Hartman, G. A. LoGrippo, "Combined beta-Propiolactone and Ultraviolet Irradiation for Plasma Sterilization", F. W. Hartman, G. A. LoGrippo, J. G. Mateer et al, eds. *Hepatitis Frontiers. Henry Ford Hosp. International Symposium,* Boston, Little, Brown & Co., (1957), 407–416; R. Kotitschke, W. Stephan, "Kominierte Behandlung von Gerinnungsfaktoren in Humanplasma mit β-Propiolacton and UV. Struktur und Funktion des Fibrinogens", H. Schroeer, G. Hauck, F. Zimmerman et al, eds., *Blutgerinnung und Mikrozirkulation Stuttgart: Verlag,* (1976), 222–228; G. A. LoGrippo, H. Hayashi, "Efficacy of beta-Propiolactone with Ultraviolet Irradiation of Hepatitis B Antigen in Human Plasma Pools, *Henry Ford Hosp. Med. J.,* (1973), 21, 181–186; D. Heinrich, H. Berthold, "Application of Cold Sterilized Prothrombin Complex Concentrates in Man: Clinical and Serological Studies", The 13th International Congress of the World Federation of Hemophilia, Tel Aviv, July 8–13, 1979; W. Stephan, A. M. Prince, "Efficacy of Combined Treatment of Factor IX Complex (PPSB) with β-Propiolactone (b-PL) and Ultraviolet (UV) Irradiation", *Haemostasis,* (1981), 10, 67; A. M. Prince, W. Stephan, B. Brotman, "β-Propiolactone/Ultraviolet Irradiation: A Review of its Effectiveness for Inactivation of Viruses in Blood Derivatives", *Rev. Infect. Dis.,* (1983), 5, 92–107; W. Stephan, A. M. Prince and R. Kotitschke, "Factor VIII Concentrate from Cold Sterilized Human Plasma", *Develop Biol. Stand,* (1983), 54, 491;

(4) heat applied to the product in the liquid state (S. S. Gellis, J. R. Neefe, J. Stokes Jr. et al, "Chemical, Clinical and Immunological Studies on the Products of Human Plasma Fractionation, XXXVI Inactivation of the Virus of Homologous Serum Hepatitis in Solutions of Normal Human Serum Albumin by Means of Heat", *J. Clin. Invest.,* (1948), 27, 239–244; R. Murray, W. C. L. Diefenbach, "Effect of Heat on the Agent of Homologous Serum Hepatitis", *Proc. Soc., Exp. Biol. Med.,* (1953), 84, 230–231; J. P. Soulier, C. Blatix, A. M. Courouce et al, "Prevention of Virus B Hepatitis (SH Hepatitis)", *Am. J. Dis. Chid.,* (1972), 123, 429–434; T. Shikata, T. Karasawa, K. Abe et al, "Incomplete Inactivation of Hepatitis B Virus After Heat-Treatment at 60° C. for 10 hours", *J. Infect. Dis.,* (1978), 138, 242–244; E. Tabor, R. J. Gerety, "The Chimpanzee Animal Model for non-A non-B hepatitis: New Applications", W. Szmuness, H. J. Alter, J. E. Maynard eds. *Viral Hepatitis: 1981 International Symposium.,* Philadelphia: The Franklin Institute Press, (1981), 305–317; Von. N. Heimburger, H. Schwinn, P. Gratz et al, "Faktor VIII-Konzentrate, Hochgereinigt und in Losung Erhitzt, *Arzneim-Thromb/Drug Res.,* (1981), 31, 619; E. Tabor, G. Murano, P. Snoy et al, "Inactivation of Hepatitis B Virus by Heat in Antithrombin III Stabilized with Citrate", *Thromb. Res.,* (1981), 22, 233–238; D. Menache, D. L. Aronson, "Measures to Inactivate Viral Contaminants of Pooled Plasma Products, R. Y. Dodd, L. F. Baker eds. *Infection Immunity and Blood Transfusion Proc. XVII Annual Scientific Symposium,* May 9–11, 1984. New York, Alan R. Loss, (1985), 407–423), or in the dry state (G. Dolana, D. Tse, W. Thomas et al, "Hepatitis Risk Reduction in Hemophilia: A Heated Factor VIII Preparation", *J. Amer. Soc. Hematol.,* (1982), 60, (Suppl 1), 2102; F. R. Hollinger, G. Dolana, W. Thomas et al, "Reduction of Infectivity of Hepatitis B Virus (HBV) and a non-A, non-B Hepatitis Agent by Heat Treatment of Human Antihemophilic Factor (AHF) Concentrates", L. R. Overby, F. Deinhardt, J. Deinhardt, eds., *Viral Hepatitis: Second International Max von Pettenkofer Symposium,* New York: Marcel Dekker, Inc., (1983) 245–246; F. B. Hollinger, G. Dolana, W. Thomas et al, "Reduction in Risk of Hepatitis Transmission by Heat-Treatment of a Human Factor VIII Concentrate", *J. Infect. Dis.,* (1984), 150, 250–262), (5) lipid solvents with the addition of surface active agents (A. M. Prince, B. Horowitz, B. Brotman et al, "Inactivation of Hepatitis B and Hutchinson Strain non-A, non-B Hepatitis Viruses by Exposure to Tween 80 and Ether", *Vox Sang,* (1984), 46, 36–43), and lipid solvents without the additive of surface active agents (S. M. Feinstone, K. B. Mihalik, T. Kamimura et al, "Inactivation of Hepatitis B Virus and non-A, non-B Hepatitis by Chloroform, *Infect. Immunol.,* (1983), 41, 816–821; D. W. Bradley, J. E. Maynard, H. Popper et al, "Posttransfusion non-A, non-B Hepatitis: Physiochemical Properties of Two Distinct Agents", *J. Infect. Dis.,* (1983), 148, 254–265); A. M. Prince, B. Horowitz, B. Brotman et al, "Inactivation of Hepatitis B Virus and non-A, non-B Hepatitis by Chloroform, *Infect. Immunol..* (1983), 41, 816–821).

Neutralization by specific antibody is limited by antibody availability (hepatitis B virus only, so far), (Tabor et al, *Lancet*, (1980), supra and Brummelhuis et al, *Vox Sang*, (1983), supra) ultraviolet irradiation and thermal inactivation methods have been variably successful (S. S. Gellis, J. R. Neefe, J. Stokes, Jr., L. E. Strong, C. A. Janeway, G. Scatchard, "Chemical, Clinical and Immunological Studies on the Products of Human Plasma Fractionation. XXXVI. Inactivation of the Virus of Homologous Serum Hepatitis in Solutions of Normal Human Serum Albumin by Means of Heat", *J. Clin. Invest.*, (1947), 27, 239–244; N. Heimburger, H. Schwinn, R. Mauler, "Factor VIII Concentrate, Hepatitis-Safe: Progress in the Treatment of Hemophilia A", *Die gelben Hefte*, (1980), 20, 165–174; M. Colombo, V. Carnelli, C. Gazengel, P. M. Mannucci, G. F. Savidge, K. Schimpf, "Transmission of non-A, non-B Hepatitis by Heat-Treated Factor VIII Concentrate", *Lancet*, (1985), July 1–4; F. E. Preston, C. R. M. Hay, M. S. Dewar, M. Greaves, D. R. Triger, "Non-A, non-B Hepatitis and Heat Treated Factor VIII Concentrates", *Lancet*, (1985), July, 213; C. Rouzioux. S. Chamaret, L. Montagnier, V. Carnelli, G. Rolland, P. M. Mannucci, "Absence of Antibodies to AIDS Virus in Haemophiliacs Treated with Heat-Treated Factor VIII Concentrate, *Lancet*, (1985), February, 271–272; P. B. A. Kernoff, E. J. Miller, G. F. Savidge, S. J. Machin, M. S. Dewar, F. E. Preston, "Wet Heating for Safer Factor VIII Concentrate?" *Lancet*, 1985, September, 721), and beta-propiolactone chemically alters proteins and its carcinogenic properties constitute a hazard to personnel handling its.

U.S. Pat. Nos. 4,481,189 and 4,540,573 describe the use of organic solvent/detergent pairs to reduce by several orders of magnitude the infectivity of hepatitis viruses and certain other viruses contained in plasma and plasma products or added thereto.

Solvent/detergent treatment under appropriate conditions of temperature and contact time effectively disassembles viruses that have envelope proteins associated with lipid, while having negligible effect on the molecular conformations and biological activities of sensitive blood plasma proteins.

The independent effects of organic solvents and detergents in disassembling and attenuating viruses can be facilitated by the presence of both. Removal of detergents, as well as organic solvents, from biologic products may be necessary, especially if a particular detergent is not well tolerated by humans or whatever biologic system within which the product is to be used.

The synthesis of certain desired biologic products can be induced or enhanced in cell cultures by introduction of phorbol esters into the culture fluid. For example, mezerein may be used to induce gamma-interferon production by cultured leukocytes (Y. K. Yip, R. H. L. Pang, J. O. Oppenheim, M. S. Nashbar, D. Henriksen, T. Zerebeckyj-Eckhardt, J. Vilcek, "Stimulation of Human Gamma Interferon Production by Diterpene Esters", *Infect. and Immun.*, (1981) 131–139) or to augment secretion of tumor necrosis factor by cells that produce it (B. D. Williamson, E. A. Carswell, B. Y. Rubin, J. S. Prendergast, H. J. Old, "Human Tumor Necrosis Factor Produced by Human B-cells Lines: Synergistic Cytoxic Interaction with Human Interferon", *Proc. Natl. Acad. Sci., USA*, (1983), 80, 5397–5401).

Before use in man, phorbol esters must be removed from lymphokine preparations because of the carcinogenic properties of these compounds. Heretofore, phorbol esters have been removed by precipitation, chromatographic, or molecular exclusion processes, (B. Y. Rubin, S. L. Anderson, S. A. Sullivan, B. D. Williamson, E. A. Carswell, L. J. Old, "Purification and Characterization of a Human Tumor Mecrosis Factor from the LukII Cell Line", *Proc. Natl. Acad. Sci., USA*, (1985), 82, 6637–6641).

Methods used to achieve removal of lipid/detergent mixed micelles from membrane protein complexes may be applicable to removal of the same from plasma products and other biologic products. These have been based on differences in size, buoyant density, charge, binding affinity, phase partitioning and solvent partitioning (A. Helenius and K. Sinous, "Solubilization of Membranes by Detergents", *Biochem. Biophys. ACTA*, (1975), 415, 29–79).

The present invention provides means for removal of virus attenuating chemicals and other lipid soluble process chemicals from biological materials by partition into innocuous natural oils or synthetic triglycerides and provides a second rationale for selecting specific solvent/detergent pairs, i.e., ease of extraction into oil, in addition to effectiveness as a virus inactivating chemical.

Use of solvent partitioning for removal of undesirable process chemicals from biologics should enable efficient removal and also assure that any residual solvent remaining in the product will not compromise its safety for parenteral administration. Use of natural or synthetic oils according to the present invention achieves these objectives and also poses no exposure hazards to personnel conducting the processes of the present invention.

In the instance of whole blood plasma, for direct use in transfusion or for subsequent fractionation, implementation of virus sterilization techniques has not been heretofore reduced to practice. Methods of heat sterilization result in unwanted protein denaturation. Immune neutralization is limited, at this time, to hepatitis B virus. Beta-propiolactone/UV treatment results in the destruction of sensitive coagulation factors, e.g., antihemophilic factor. Organic solvent/detergent mixtures require implementation of expensive and inconvenient fractionation steps to remove the reagents which cannot be applied conveniently to single units of plasma intended for transfusion or to plasma pools.

Thus, because virus sterilization techniques have not been applied to whole blood plasma, virus infectivity upon infusion remains, estimated at 0.05% for hepatitis B and 3% for non-A, non-B hepatitis transmission

SUMMARY OF THE INVENTION

It is an object of the present invention to remove virus inactivating solvents and/or certain detergents and/or phorbol esters from biologic materials, while avoiding the use of environmentally or physiologically hazardous reagents. This object and other objects are provided by the present invention wherein lipid soluble process chemicals, e.g., virus inactivating solvents and/or certain detergents and/or phorbol esters, are extracted using a naturally occurring oil extracted from a plant or an animal or a synthetic compound of similar chemical structure, i.e., oils that are neither flammable, nor explosive, nor incompatible with parenterally administered biologics and blood derivatives. The oil should be pharmaceutically and physiologically tolerated by a patient. Any traces of extracting fluid inadvertently remaining in the product would generally not adversely affect the suitability of the product for infusion into a human, e.g., by parenteral administration.

The present invention concerns methods for removing virus attenuating solvents from biological materials to which such solvents have been added. The present invention also concerns removal of certain virus attenuating detergents from biological materials to which such detergents have been added together with or without solvents.

The present invention also concerns methods for the removal of lymphokine inducing phorbol esters from biological materials to which phorbol esters have been added together with or without virus attenuating solvents and/or detergents.

The present invention further concerns methods for single or multiple extractions of solvents, certain detergents and phorbol esters from biological materials by using edible oils or triglycerides, in which the extractants rapidly and preferentially enter the oil phase.

The present method involves bringing the biological materials containing the lipid soluble process chemicals, e.g., virus attenuating solvents and/or detergents and/or phorbol esters, into contact with an effective amount of a naturally occurring oil extracted from a plant or an animal or a synthetic compound of similar chemical structure. Thereafter, the resultant mixture is agitated and phase separation occurs by sedimentation or can be facilitated by centrifugation. The upper phase contains oil and extracted process chemicals. The lower phase is relatively free of process chemicals and contains product.

The present invention also concerns whole blood plasma wherein virus is inactivated, blood protein biological activity necessary for use is retained and added virucidal compounds are removed to the extent of 95% or more.

The present invention is thus also directed to a blood plasma or blood serum having an extent of inactivation of virus greater than 4 logs for said virus, having at least 45% retention of functional activity for particular biologically active blood proteins (e.g. Factor VIII), and having no more than physiologically acceptable levels of lipid soluble process chemicals. The retention of functional activity is relative to untreated blood, blood plasma or blood serum. The protein composition of the plasma is unchanged (same as if untreated), as measured by cellulose acetate electrophoresis. If, for example, the lipid soluble process chemical is TNBP, the physiologically acceptable levels of TNBP are 1 to 10 ppm. Such physiologically acceptable levels, however, vary depending on the particular lipid soluble process chemical. The lipid soluble process chemicals (added viricidal agents) are removed to the extent of 95% or more. In other words, after treatment of plasma to inactivate virus, the present invention provides for the extraction of harmful solvents used in the virus inactivation in order to produce a safe plasma wherein its therapeutic efficacy is retained.

The present invention also includes protein compositions made from virus sterilized whole plasma.

BRIEF DESCRIPTION OF THE DRAWINGS

FIG. 1 is a graph showing TNBP in a plasma fraction containing AHF after oil extraction (three extractions using 20%, 10% and 5% ((v/v) oil).

FIG. 2 is a graph showing inactivation of VSV added to AHF by TNBP/"TRITON X 45".

DETAILED DESCRIPTION OF THE INVENTION

Blood is made up of solids (cells, i.e., erythrocytes, leucocytes, and thrombocytes) and liquid (plasma). The cells contain potentially valuable substances such as hemoglobin, and they can be induced to make other potentially valuable substances such as interferons, growth factors, and other biological response modifiers. The plasma is composed mainly of water, salts, lipids and proteins. The proteins are divided into groups called fibrinogens, serum globulins and serum albumins. Typical antibodies (immune globulins) found in human blood plasma include those directed against infectious hepatitis, influenza H, etc.

Blood transfusions are used to treat anemia resulting from disease or hemorrhage, shock resulting from loss of plasma proteins or loss of circulating volume, diseases where an adequate level of plasma protein is not maintained, for example, hemophilia, and to bestow passive immunization.

Whole blood must be carefully typed and cross matched prior to administration. Plasma, however, does not require prior immunological testing. For certain applications, only a proper fraction of the plasma is required, such as factor VIII for treatment of hemophilia or von Willebrand's disease.

With certain diseases one or several of the components of blood may be lacking. Thus the administration of the proper fraction will suffice, and the other components will not be "wasted" on the patient; the other fractions can be used for another patient. The separation of blood into components and their subsequent fractionation allows the proteins to be concentrated, thus permitting concentrates to be treated. Of great importance, too, is the fact that the plasma fractions can be stored for much longer periods than whole blood and they can be distributed in the liquid, the frozen, or the dried state. Finally, it allows salvaging from blood banks the plasma portions of outdated whole blood that are unsafe for administration as whole blood.

Proteins found in human plasma include prealbumin, retinol-binding protein, albumin, alpha-globulins, beta-globulins, gamma-globulins (immune serum globulins), the coagulation proteins (antithrombin III, prothrombin, plasminogen, antihemophilic factor (factor VIII), fibrin-stabilizing factor-factor XIII, fibrinogen), immunoglobins (immunoglobulins G, A, M, D, and E), and the complement components. There are currently more than 100 plasma proteins that have been described. A comprehensive listing can be found in "The Plasma Proteins", ed. Putnam, F. W., Academic Press, New York (1975).

Proteins found in the blood cell fraction include hemoglobin, fibronectin, fibrinogen, enzymes of carbohydrate and protein metabolism, etc. In addition, the synthesis of other proteins can be induced, such as interferons and growth factors.

A comprehensive list of inducible leukocyte proteins can be found in Stanley Cohen, Edgar Pick, J. J. Oppenheim, "Biology of the Lymphokines", Acamedic Press, N.Y. (1979).

Blood plasma fractionation generally involves the use of organic solvents such as ethanol, ether and polyethylene glycol at low temperatures and at controlled pH values to effect precipitation of a particular fraction containing one or more plasma proteins. The resultant supernatant can itself then be precipitated and so on until the desired degree of fractionation is attained. More recently, separations are based on chromotographic processes. An excellent survey of blood fractionation appears in *Kirk-Othmer's Encylopedia of Chemical Technology,* Third Edition, Interscience Publishers, Volume 4, pages 25 to 62.

The major components of a cold ethanol fractionation are as follows:

| Fraction | Proteins |
| --- | --- |
| I | fibrinogen; cold insoluble globulin; factor VIII; properdin |
| II and III | IgG; IgM: IgA; fibrinogen; beta-lipoprotein; prothrombin; plasminogen; plasmin inhibitor; factor V; factor VII; factor IX; factor X: thrombin; antithrombin; isoagglutinins; ceruloplasmin; complement C'1, C'3 |
| IV-1 | alpha$_1$-lipoprotein, ceruloplasmin; plasmin-inhibitor; factor IX; peptidase; alpha-and-beta-globulins |
| IV-4 | transferrin; thyroxine binding globulin; serum esterase; alpha$_1$-lipoprotein; albumin; alkaline phosphatase |
| V | albumin; alpha-globulin |
| VI | alpha$_1$-acid glycoprotein; albumin |

The above fractionation scheme can serve as a basis for further fractionations. Fraction II and III, for example, can be further fractionated to obtain immune serum globulin (ISG).

Another fractionation scheme involves use of frozen plasma which is thawed into a cryoprecipitate containing AHF (antihemophilic factor) and fibronectin and a cyrosupernatant. The cryoprecipitate is then fractionated into fibronectin and AHF.

Polyethylene glycol has been used to prepare high purity AHF and non-aggregated ISG.

High risk products with respect to the transmission of hepatitis B and non-A, non-B are fibrinogen, AHF and prothrombin complex, and all other blood protein preparations except immune serum globulin and, because they are pasteurized, albumin solutions.

The methods of the present invention are applicable to biological materials including blood plasma, blood fractions thereof, and blood proteins such as those discussed hereinabove.

Examples of naturally occurring oils extracted from a plant (vegetable, fruit, nut, seed, bean, etc.) or an animal (including fish), i.e., fats and fatty oils, e.g., edible oils, for use in the present invention include soybean and safflower oils, both of which are ingredients of U.S. FDA licensed hyperalimentation fluids for intravenous administration. These preparations are tolerated with no adverse reactions at levels up to 5 g/kg body weight per day during prolonged treatment periods. Thus, vegetable oils thay may persist in extracted plasma protein preparations are expected to be innocuous in contrast to residual TNBP in parenteral therapeutics, part of which (up to 4%) may be metabolized to form butanol, wnhich is likely to accumulate and cause neurotoxicity.

Other non-limiting examples of edible vegetable oils for use in the present invention include ricin oil (castor oil), cottonseed oil, corn oil, safflower oil, sesame oil, sunflower seed oil, almond oil, apricot kernel oil, coconut oil, cocoa butter, grapefruit seed oil, linseed oil, mustard seed oil, orange seed oil, palm oil, palm kernel oil, poppyseed oil, rice bran oil, sorghum oil, walnut oil, wheat germ oil, kapok oil, hempseed oil, peanut oil and olive oil. Non-limiting example of animal derived oils for use in the present invention include cow butterfat, goat butterfat, lard, tallow and neatsfoot oil. Furthermore, comparable edible oils derived from fish, e.g., whale oil, cod liver oil, herring oil, sardine oil, menhaden oil and seal oil, or non-toxic mineral oils, etc., may also be used in the present invention for extraction of a variety of virus attenuating organic solvents and/or detergents and/or phorbol esters. Synthetic compounds having similar chemical structures to the aforesaid oils can also be used. A particularly preferred synthetic compound is a synthetic triglyceride. Non-limiting examples of synthetic triglycerides for use in the present invention include triolein, tristearin, tripalmitin, trimyristin, and combinations thereof. Particularly preferred is triolein which is pure or a highly defined chemical prepared synthetically from glycerol and oleic acid or from glycerol and defined fatty acid mixtures and is liquid at room temperature. It is also contemplated that synthetic diglycerides and synthetic monoglycerides can be utilized.

The oil for use in the present invention can be any glyceride-containing oil that would be physiologically tolerated.

The lipid soluble process chemicals according to the present invention are ones that are readily extracted from an aqueous solution by using the oils of the present invention.

Although the present invention is applicable to extraction of a wide variety of solvents from biological materials, the method is particularly suitable for removal of higher boiling solvents.

The use of higher boiling solvents for virus attenuation and removal of these after sufficient contact time by extraction into edible oils avoids the hazards of using flammable solvents altogether whether in the attenuation process or in the process of removing attenuators.

A dialkylphosphate or a trialkylphosphate having branched or unbranched, substituted or unsubstituted alkyl groups which contain 1 to 10 carbon atoms, especially 3 to 30 carbon atoms and more particularly 2 to 10 carbon atoms can be used in the present invention. Illustrative members of trialkylphosphates for use in the present invention include tri-(n-butyl)phosphate, tri-(t-butyl)phosphate, tri-(n-hexyl)phosphate, tri-(2-ethylhexyl)phosphate, tri-(n-decyl)phosphate, just to name a few. An especially preferred trialkylphosphate is tri-(n-butyl)phosphate. Mixtures of different trialklyphosphates or mixed alkyl phosphates can also be used. Similarly, the respective dialkylphosphates can be employed, including those of different alkyl group mixtures of dialkylphosphate. Furthermore, mixtures of di- and trialkylphosphates can be employed.

Di- or trialkylphosphates for use in the present invention are employed in an amount between about 0.01 mg/ml and about 100 mg/ml, and preferably between about 0.1 mg/ml and about 10 mg/ml.

Virus attenuating solvents that can be removed by the method of the present invention may be used alone for virus inactivation or in the presence of detergents that may not be extractable by methods for solvent removal, as well as those detergents that are extractable. Other lipid soluble process chemicals including diterpene esters may be used in similar combinations or alone.

The di- or trialkylphosphate can be used with or without the addition of wetting agents. It is preferred, however, to use di- or trialkylphosphate in conjunction with a wetting agent. Such wetting agent can be added either before, simultaneously with, or after the di- or trialkylphosphate contacts the blood biological material, e.g., protein-containing composition. The function of the wetting agent is to enhance the contact of the virus in the biological material, e.g., blood protein-containing composition, with the di- or trialkylphosphate. The wetting agent alone may or may not adequately inactivate the virus.

Contemplated non-ionic detergents for use in the present invention include those which disperse at the prevailing temperature at least 0.1% by weight of the surfactant in an aqueous solution containing the same when introduced therein. In particular there are contemplated detergents which include polyoxyethylene derivatives of fatty acids, partial esters of sorbitol anhydrides, for example, those products known commercially as "TWEEN 80", "TWEEN 10" and "POLYSORBATE 80" and non-ionic oil soluble water detergents such as that sold commercially under the trademark "TRITON X 100", TRITON X 114" and "TRITON X 45" (oxyethylated alkylphenols). Also contemplated are bile salts such as sodium cholate, as well as the "Zwittergents" which are synthetic zwitterionic detergents known as "sulfobetaines", such as N-dodecyl-N, N-dimethyl-2-amino-1 ethane sulphonate and its congeners or non-ionic detergents such as octyl-beta-D-gluco-pyranoside.

Surfactants for use in the present invention may poorly, modestly, or avidly partition into the oil phase when oil is admixed with an aqueous solution containing the desire protein biologic together with surfactant.

Preferred surfactants for use in the present invention are those having extraction coefficients favoring transfer from aqueous to oil phase with greater than 80% efficiency when the volume of the oil phase is not greater then 20% of the volume of the aqueous phase.

Such extractable detergents include, but are not limited to, "TRITON X 45", whereas "TRITON X 110" is not efficiently removable by oil extraction and "TRITON X 114" is marginally removable at the 90% efficiency level, when the volume of extraction oil is 20% of the aqueous volume.

However, less efficient extractions of detergent are contemplated in accordance with the present invention by repeating extractions or by using counter flow extraction techniques until desired levels of detergent have been achieved in the product. Thus, it is contemplated that a variety of detergents may be employed including, but not limited to "TRITON" (octoxanol), nonoxanols, "TWEENS", glucopyranosides, etc.

Treatment of blood protein-containing compositions with trialkylphosphate is effected at a temperature between −5° C. and 70° C., preferably between 0° C. and 60° C. The time of such treatment (contact) is for at least 1 minute, preferably at least 1 hour and generally 4 to 24 hours. The treatment is normally effective at atmospheric pressure, although subatmospheric and superatmospheric pressures can also be employed.

Exemplary ranges for solvent, detergent and oil are as follows:

Solvent: 1000–10,000 ppm

Detergent: 1000–10,000 ppm

Oil: 5–50% of biological fluid (weight %)

The preferred ranges for each of the above is lowest possible value commensurate with effective virus inactivation and quantitative extraction of solvent and detergent.

Normal and preferred extraction conditions are as follows:

normal: ambient temperature to 35° C., preferred: ambient, normal exposure time: 10–60 minutes;

preferred: 30 minutes.

The present invention is particularly directed, inter alia, to producing a blood plasma protein-containing composition such as blood, blood plasma, blood plasma fractions, etc., which is substantially free of infectious virus, yet which contains a substantial amount of enzymatically or biologically active (undenatured) protein. More particularly, the present invention is directed to inactivation of lipid-containing virus and preferentially inactivation of AIDS virus (HTLV III/LAV) and hepatitis B, and non-B non-A (NANB) hepatitis virus. Other viruses inactivated during the course of the present invention include, for example, cytomegaloviruses, Epstein Barr viruses, lactic dehydrogenase viruses, herpes group viruses, rhabdoviruses, leukoviruses, myxoviruses, alphaviruses, arboviruses (group B), paramyxoviruses, arenaviruses, coronaviruses, retroviruses including HTLV III/LAV, and animal leukemia viruses.

Biological fluids for use according to the present invention include mammalian blood, blood plasma, blood plasma fractions, precipitates from blood fractionation and supernatants from blood fractionation, platelet concentrates, white cell (leukocyte) concentrates, and leukocyte-poor packed red cells, as well as platelet rich plasma and platelet poor plasma, including packed cell masses comprising the white buffy coat consisting of white blood cells above packed red cells. Also contemplated is the treatment of masses containing concentrates of granulocytes, monocytes, cells capable of producing interferon, tissue necrosis factor and other immune modulators and lymphokines or media separated from such concentrates or suspensions.

Inactivation of virus is obtained by use of the present invention to the extent of at least "4 logs", i.e., virus in a serum is totally inactivated to the extent determined by infectivity studies where that virus is present in the untreated serum in such a concentration that even after dilution to $10^4$, viral activity can be measured.

According to the present invention, there is contemplated a protein-containing composition, particularly whose blood plasma or whole blood serum having an extent of inactivation of virus greater than 4 logs of virus, such as AIDS virus, hepatitis B virus and non-A and non-B hepatitis virus, having a retention of functional activity for particularly biologically active proteins of at least 45%, preferably at least 75%, more preferably at least 85%, even more preferably at least 95% and most preferably 98% to 100%, and having no more than physiologically acceptable levels of lipid soluble process chemicals.

The (virus sterilized) whole blood plasma or blood serum according to the present invention can be transfused directly into a human patient. Alternatively, the (virus sterilized) whole blood plasma or blood serum according to the present invention can be fractionated to prepare purified plasma protein derivatives (such derivatives can be transfused directly into a human patient).

The whole blood plasma or blood serum according to the present invention can also be used in cell cultures and as a quality control reagent.

Furthermore, non-blood sources including, for example, normal or cancer cells, exudate from cancer or normal cells grown in culture, hybridomas and products from gene splicing, plant cell concentrates or suspensions, extracts of animal or plant tissues, or microorganisms can be used as the biological fluid in the present invention.

The present invention will now be described with reference to the following non-limiting examples.

EXAMPLES

Example 1

TNBP (Tri-n-Butylphosphate) Extraction from Aqueous AHF Concentrate

TNBP from Fisher Scientific, Pittsburgh, PA, USA was added to aqueous AHF concentrate in excess and thrice extracted with 5, 10, or 15% (v/v) soybean oil. TNBP remaining in the aqueous phase is represented by FIG. 1.

Example 2

Extractable and Non-Extractable Detergents

Detergent solutions were twice extracted with equal volumes of soybean oil at ambient temperature. The results of Example 2 as summarized hereinbelow in Table 1.

TABLE 1

| Detergent | % Remaining in Aqueous Phase | Extraction |
|---|---|---|
| "TWEEN 80" (from ICI Americas) | 80 | poor extraction |
| "TRITON X 114" (from Rohm & Haas, Philadelphia, PA, USA) | 19 | good extraction |
| "TRITON X 45" (from Rohm & Haas) | <2 | excellent extraction |
| n-Dodecylgluco-pyranoside (from Sigma Chemical Co., St. Louis, MO, USA) | 19 | good extraction |

The above Example 2 demonstrates a one-step removal of both solvent and detergent.

Example 3

Extraction of Mezerein from Cell Culture Media Using Soybean Oil

| Materials | Supplier |
|---|---|
| Soybean oil | Penta International, West Caldwell, NJ, USA |
| Mezerein | Meloy Laboratories |
| RPMI-1640 | Gibco Laboratories |
| LuKII cells | |

Five tubes were set up to contain 4 ml of the following:
(1) 10 μg/ml of mezerein in RPMI
(2) 10 μg/ml of mezerein in RPMI
(3) 1 μg/ml of mezerein in RPMI
(4) 1 μg/ml of mezerein in RPMI
(5) RPMI 1 ml of soybean oil was added to tubes 1, 3 and 5 and the tubes were shaken vigorously for 15 seconds. The tubes were then allowed to stay undisturbed for 15 minutes, at which time the oil was removed. This treatment was repeated two additional times. Sample 5 was then divided in half and half was supplemented to contain 10 μg/ml of mezerein and the other half 1 μg/ml of mezerein. These two samples (termed 5a and 5b) were prepared to determine whether the oil extraction altered the media in any way so as to inhibit the production of TNF by the cells. Samples 2 and 4 which were not exposed to oil, were shaken for a total of 45 seconds to ascertain whether shaking affects the ability of the preparation to induce the cells to produce TNF.

All samples were then diluted so that if the treatments had no effect on the mezerein, cultures of the LuKII cells would contain 10 ng/ml of mezerein. All cultures were set-up in duplicate and each culture was assayed in triplicate. Mean values for 6 numbers obtained are being presented. Please note that the LuKII cells produce TNF spontaneously in the absence of mezerein. The amount of TNF produced in the absence of mezerein by the LuKII cells in this experiment was 128 units/mL.

The results for Example 3 are given hereinbelow in Table 2.

TABLE 2

| Sample No. | Mean TNF Titer Units/mL | Titer Above No Mezerein Background |
|---|---|---|
| 1 | 145 | 17 |
| 2 | 438 | 310 |
| 3 | 163 | 35 |
| 4 | 267 | 139 |
| 5a | 270 | 142 |
| 5b | 368 | 240 |

Conclusion: Soybean oil is capable of extracting mezerein from RPMI media.

Example 4

Virus Inactivation of AHF Concentrate with TNBP/TRITON X 45 and Reagent Removal by Extraction with Soybean Oil Greater than $10^{4.5}$ infectious units of vesicular stomatitis virus was added to AHF concentrate solutions containing 0.1% "TRITON X 45" with and without 0.3% TNBP. The detergent alone killed greater than $10^{3.5}$ units of virus infectivity within 1 hour at 24° C. and detergent plug 0.3% TNBP completely abolished infectivity within the same time. Extraction with 20% soybean oil (v/v) removed greater than 96% of the "TRITON X 45", as well as the TNBP wwith retention of greater than 85% of the Antihemophilic Factor activity. The results for Example 4 are given in FIG. 2.

Example 5

Virus Inactivated Single Donor Plasma

Plasma harvested from donated blood in the presence of anticoagulants and transferred to a satellite container, is treated by aseptic addition of solvent or solvent and detergent pairs. The detergent employed should be tolerated at least at the concentrations employed without adverse side reactions when administered intravenously. The solvent is used alone or the solvent/detergent pair as demonstable by in vitro or in in vivo assays for virus inactivation must be capable of attenuating contaminating virions sufficiently to render them noninfective.

Blood collected into anticoagulant solution was sedimented and about 100 cc of the supernatant plasma was transferred to a flask containing test virus suspensions. A virus attenuating organic solvent was added and finely dispersed by stirring. In this example, the solvent was TNBP 2%. After exposure for four hours at 37° C., the TNBP was extracted into 20 ml cottonseed oil U.S.P. by shaking then separating the phases by sedimentation and decanting the upper-phase. The lower phase plasma was analyzed for virus infectivity and for labile clotting factors.

Results:

| | |
|---|---|
| Residual TNBP in plasma | <0.3 ppm |
| Virus inactivation: | |
| HTLV-III | non-infective in H9 cells |
| VSV | $10^{4.5}$ infectious units killed within 1 hour |
| Coagulation Factor Activity Retained: | |
| Prothrombin | >89% |
| Factor VII activity | >70% |
| Factor V activity | $\geq$56% |
| Factor IX activity | $\geq$80% |
| Antithrombin III activity | $\geq$95% |
| Cellulose Acetate Electrophoresis: | |
| Normal distribution of plasma proteins | |
| Fibrinogen | 5.0–8.0% |
| alpha-1-globulins | 2.5–3.1% |
| alpha 2 globulins | 8.0–10.0% |
| beta globulins | 8.0–11.0% |
| gamma globulins | 8.0–10.0% |
| albumin | 58–65% |

Example 6

Removal of Virus Inactivating Reagents from AHF Enriched Cryoprecipitate of Plasma Frozen plasma when thawed at temperatures just slightly above the freezing point forms a gelatinuous residue (cryoprecipitate) rich in antihemophilic factor. This material when administered intravenously is capable of correcting congenital deficiencies of two inherited types; hemophilia and Von Willebrand's factor deficiency with attendant risks of viral disease transmission.

Frozen plasma cryoprecipitate harvested from approximately 250 cc plasma units separated from approximately 450 ml voluntary blood donations in anticoagulation solution were individually thawed into normal saline at 50 ml ambient temperature, then continuously admixed with 250 mg "TRITON X 45" and 0.75 ml TNBP for 5 hours. This virus attenuating chemicals were twice extracted into 10 ml cottonseed oil.

Results: (average of 4 experiments)

The aqueous phase contained less than 3 ppm TNBP and greater then 97% of the "TRITON X 45" had partitioned into the sequential oil phases. AHF procoagulant activity remaining in the aqueous phase ranged from 80–150 international units.

Promotion of platelet aggregation in the presence of ristocetin, a requisite though insufficient indicator of VWF activity, appeared to be normal.

Example 7

Extraction Of TNBP From Virus Inactivated Hepatitis B Immune Globulin

Immune globulin ("HBIG" from Cutter Laboratories) was diluted 1.5 fold wwith distilled water. TNBP was added 1:100 w/w continuously admixed at ambient temperature for 4 hours and then thrice extracted with 20% (v:v) soybean oil. Residual TNBP in the aqueous phase was less than 0.5 ppm, while hepatitis B antibody activity as determined by a commercially available test (Ausab), when corrected for dilution and decantation volume losses, was unchanged.

Example 8

Extraction Of TNBP From Intravenous Immune Serum Globulin (IVISG)

IVISG Sandoz, Hanover, N.J., USA, ("SANDO-GLUBULIN") is reconstituted with 4/5 volume distilled water. TNBP is added (1:100 w/w) and is finely dispersed by shaking for six hours at 30° C. Then 1/5 volume of soybean oil is dispersed finely into the mixture, permitted to separate and decanted. Finally, 1/5 volume distilled water is added.

Results: TNBP level in product is less than 0.5 parts per million.

Example 9

Extraction Of TNBP Added To Pooled Plasma

TNBP (1 g/100 cc) was added to pooled plasma and finely dispersed by stirring. One-tenth volume of soybean oil was then finely dispersed into the mixture. Stirring was stopped to permit the phases to separate and the oil layer was decanted. A second and third extraction and decantation were performed and TNBP levels were assayed at each stage. The results for this example are as follows:

| | ppm |
|---|---|
| TNBP added | 10,000 |
| dissolved TNBP | 500 |
| first extraction TNBP | 40 |
| second extraction TNBP | 2 |
| third extraction TNBP | 0.1 nondetectable |

Example 10

Extraction Of TNBP In The Production OF Virus Inactivated AHF Concentrate

Pooled cryoprecipitate of plasma was extracted with an aqueous solution containing heparin and ionized calcium. The pH was adjusted to 6.4 and the temperature was adjusted to 10° C. forming a precipitate which was centrifugally separated and discarded. The supernate after aluminum hydroxide adsorption was exposed to 0.3% w/v TNBP/0.2% sodium cholate for six hours at 30° C. with stirring. Soybean oil (0.05 vol:vol) was finely dispersed into the mixture—the phases were separated, the oil layer was removed. The aqueous phase contained less than 20 ppm of the added 3,000 ppm TNBP.

The volume of aqueous phase was reduced by semipermeable membrane filtration and then passed through a molecular exclusion column of gel ("SEPHADEX G25").

The effluent TNBP level associated with effluent AHF activity was 0.5 ppm/30 IU AHF.

Example 11

Virus Inactivated Serum

Plasma from donated blood was recalcified and allowed to clot overnight. The resultant serum was 37° C. for 5 hours. Added TNBP was removed by twice extracting with 20% soybean oil and the aqueous phase was filtered, ultimately with a 0.2 micron sterilizing filter. The growth promoting properties of the resultant virus sterilized serum were assessed using LukII cells by comparison to LukII cells grown in the presence of serum not treated to inactivate virus. In addition, the residual level of TNBP was measured and parallel studies were conducted to determine virus kill.

| Results: | Sindbis Virus Kill: | 1 hour | >5.1 logs |
|---|---|---|---|
| | | 5 hours | >5.1 logs |
| TNBP in serum: | | | |
| start | | | 20,000 ppm |
| end | | | $\leq$ 10 ppm |
| % removed | | | $\geq$ 99.95% |
| Cellulose Acetate Electrophoresis: | | | |
| fibrinogen | | | <0.5% |
| alpha-1-globulin | | | 3% |
| alpha-2-globulin | | | 10% |
| beta-globulin | | | 10% |
| gamma-globulin | | | 10% |
| albumin | | | 67% |

Growth Promotion:

| | Cell Number | |
|---|---|---|
| Incubation (hours) | RPMI 1640 + 8% Untreated Serum | RPMI 1640 + 8% Virus Sterilized Serum |
| Start | $1 \times 10^5$ | $1 \times 10^5$ |
| 24 | $0.5 \times 10^5$ | $0.9 \times 10^5$ |
| 48 | $2 \times 10^5$ | $1 \times 10^5$ |
| 72 | $4 \times 10^5$ | $2 \times 10^5$ |
| 120 | $10 \times 10^5$ | $17 \times 10^5$ |

Example 12

Virus Inactivated Serum as a Clinical Control Reagent

Virus sterilized serum, prepared as described in Example 11, was analyzed and compared with the initial, untreated serum. The results are as follows:

| Biochemical Indicator | Untreated Serum | Virus Sterilized Serum |
|---|---|---|
| Protein (g/dl) | 5.4 | 5.3 |
| Albumin (g/dl) | 3.6 | 3.5 |
| Globulin (g/dl) | 1.8 | 1.8 |
| Alkaline phosphatase | 39 | 45 |
| SGOT | 4 | 8 |
| SGPT | 5 | 8 |
| LDH | 131 | 143 |
| GGT | 16 | 16 |
| CPK | 106 | 93 |
| Cholesterol | 160 | 68 |

It will be appreciated that the present specification and claims are set forth by way of illustration and not limitation and that various modifications and changes may be made without departing from the spirit and scope of the present invention.

What is claimed is:

1. A method of removing lipid soluble process chemicals from biological materials comprising blood plasma and fractions thereof containing said lipid soluble process chemicals, said lipid soluble process chemical being a virus attenuating solvent having a high flash point, a detergent, or a mixture thereof, comprising bringing said biological materials containing said lipid soluble process chemicals into contact with an effective amount of a naturally occurring oil extracted from a plant or an animal or a synthetic compound of similar chemical structure so as to remove 80% or more of said lipid soluble process chemicals, the oil being nonflammable, nonexplosive, compatible with parenterally administered biologics and blood derivatives and pharmaceutically and physiologically tolerable by a human, agitating the resultant mixture, separating out an upper-phase and a lower-phase by sedimentation or centrifugation and decanting the upper-phase.

2. A method according to claim 1, wherein said oil is selected from the group consisting of soybean oil, safflower oil, ricin oil, cottonseed oil, corn oil, peanut oil, olive oil, whale oil and cod liver oil.

3. A method according to claim 1, wherein said lipid soluble process chemical is a virus attenuating solvent.

4. A method according to claim 3, wherein said solvent is N-tributylphosphate.

5. A method according to claim 3, wherein the virus attenuating solvent is utilized in conjunction with a detergent.

6. A method according to claim 1, wherein the lipid soluble process chemical is a phorbol ester.

7. A method according to claim 1, wherein the phorbol ester is a diterpene ester.

8. A method according to claim 1, wherein the synthetic compound is a synthetic triglyceride and is selected from the group consisting of tristearin, tripalmitin, triolein, trimyristin and combinations thereof.

9. A method according to claim 1, wherein the biological material is selected from the group consisting of blood plasma, blood serum, Fraction I, Fraction II, Fraction III, Fraction IV-1, Fraction IV-4, Fraction V, Fraction VI, fibronectin, antihemophilic factor, prealbumin, retinol-binding protein, albumin, alpha-globulins, beta-globulins, gamma globulins, antithrombin III, prothrombin, plasminogen, fibrinogen, factor XIII, immunoglubin G, immunoglubin A, immunoglubin M, immunoglubin D and immunoglubin E, plasmin inhibitor, prothrombin, thrombin, antithrombin, factor V, factor VII, factor VIII, factor IX and factor X.

10. A method according to claim 1, wherein the oil is contained in an amount of 5 to 50 weight %, based on the weight of the biological fluid.

11. A method of removing lymphokine inducing phorbol esters from lymphokine-containing biological materials selected from the group consisting of mammalian blood, platelet concentrates, white cell concentrates, concentrates of granulocytes, concentrates of monocytes, suspension of cells capable of producing interferon, suspension of cells capable of producing tissue necrosis factor, suspension of cells capable of producing other immune modulators and lymphokines, media separated from said concentrates and suspensions, exudate from cancer cells, exudate from normal cells grown in culture, hydridomas, products from gene splicing, plant cell concentrates, plant cell suspensions, extract of animal tissues, extracts of plant tissues and microorganisms, comprising bringing said biological materials containing said phorbol esters into contact with an effective amount of a naturally occurring oil extracted from a plant or an animal or a synthetic compound of similar chemical structure so as to remove 80% or more of the phorbol esters, the oil being nonflammable, non explosive, compatible with parenterally administered biologics and blood derivatives and pharmaceutically and physiologically tolerable by a human, agitating the resultant mixture, separating out an upper-phase and a lower-phase by sedimentation or centrifugation and decanting the upper-phase.

12. A method according to claim 11, wherein said oil is selected from the group consisting of soybean oil, safflower oil, ricin oil, cottonseed oil, corn oil, peanut oil, olive oil, whale oil and cod liver oil.

13. A method according to claim 11, wherein the phorbol ester is a diterpene ester.

14. A method according to claim 11, wherein the synthetic compound is a synthetic triglyceride and is selected from the group consisting of tristearin, tripalmitin, triolein, trimyristin and combinations thereof.

* * * * *

UNITED STATES PATENT AND TRADEMARK OFFICE
CERTIFICATE OF CORRECTION

PATENT NO. : 4,789,545
DATED : Dec. 6, 1988
INVENTOR(S) : Woods et al.

It is certified that error appears in the above-identified patent and that said Letters Patent is hereby corrected as shown below:

Col. 9, line 36  Delete "coefficients" and substitute --coefficiencies--

Col. 14, line 61  Insert --treated to inactivate virus by exposure to 2% TNBP and-- after "was"

Signed and Sealed this

Ninth Day of January, 1990

Attest:

JEFFREY M. SAMUELS

Attesting Officer  Acting Commissioner of Patents and Trademarks